United States Patent [19]

Schaldach

[11] Patent Number: 4,873,980

[45] Date of Patent: Oct. 17, 1989

[54] HEART PACEMAKER

[75] Inventor: Max Schaldach, Erlangen, Fed. Rep. of Germany

[73] Assignee: Mess-und Therapiegeräte GbmH & Co., Berlin, Fed. Rep. of Germany

[21] Appl. No.: 26,674

[22] Filed: Mar. 17, 1987

Related U.S. Application Data

[63] Continuation-in-part of Ser. No. 908,367, Sep. 17, 1986, abandoned.

[30] Foreign Application Priority Data

Sep. 17, 1985 [DE] Fed. Rep. of Germany ....... 3533502

[51] Int. Cl.$^4$ .............................................. A61N 1/36
[52] U.S. Cl. .................................................. 128/419
[58] Field of Search ................................. 125/119 PG

[56] References Cited

U.S. PATENT DOCUMENTS 4,527,568  7/1985  Rickards ...................... 128/419 PG
4,535,774  8/1985  Olson .......................... 128/419 PG

FOREIGN PATENT DOCUMENTS 2026870  2/1980  United Kingdom ......... 128/419 PG Primary Examiner—William E. Kamm
Attorney, Agent, or Firm—Spencer & Frank

[57] ABSTRACT

A cardiac pacer features plural addressable digital memory elements each containing different pulse parameters for the pacing stimulation, address-selecting digital logic circuitry for choosing the characteristics of the pulses to be generated in response to signals derived from plural physiological sensors detecting different exercise-related body functions to improve control of the heart during various levels of exertion.

10 Claims, 12 Drawing Sheets

HEART PACEMAKER

CROSS REFERENCE TO RELATED APPLICATION

This application is a continuation-in-part of Ser. No. 06/908,367, filed Sept. 17th, 1986, now abandoned.

BACKGROUND OF THE INVENTION

The present invention relates to a cardiac pacemaker of the type defined by the preamble to claim 1.

In pacemakers, the attempt has been made for some time for the adaptation of the pacing to physiological conditions not only to be related to timing of the pacing pulses within the heart cycle defined by the basic rate, but for the pacing rate itself and thus the available cardiac output to be tailored to the needs of the patient. The previous timing variation of the pacing pulses, in contrast, was characterized primarily by the attempt to avoid competition between the artificial pacing and spontaneous action.

SUMMARY OF THE INVENTION

From German patent DE-A-31 04 938 or European patent A-0 140 472, physiologically controlled cardiac pacemakers are known in which a pacing parameter (AV interval or basic pacing rate) is determined by measured variables picked up in the heart of the patient and which vary the pacing behavior as a function of performance.

A disadvantage here is that the measured values that are picked up cannot be varied in terms of their effect on cardiac behavior, and in particular only a simple linear relationship is available, without taking into account the effects of other parameters. The causal connections in evaluating measured variables in the body for performance-related pacing are contrarily much more complicated than is often assumed. The linkages are entirely non-linear in nature, and their outcome is often not foreseeable at the outset because may intracorporeal processes of compensation, adaptation and control are superimposed on one another. Above all, it proves to be extraordinarily difficult to formulate these linkages in a closed functionally representable algorithm. This also fails to take into account the fact that pathological changes necessitate individual adaptations, and solutions of general validity are only limitedly applicable, if at all. Nor can it be forgotten that if the sinus rhythm, as a natural performance-related control variable for the heart rate, is absent, then substantial pathological damage is already present.

In the above-mentioned known solutions, which are oriented to a monotonous connection between the measured variable and the output variable, the existence of a relative maximum on the control characteristic curve used already leads to failure.

Moreover, introducing physiological measured variables in the signal processing in the pacemaker already entails difficulties because the programming and the adjustments that must be made for this purpose are as a rule very difficult for the attending physician to supervise, and complex decisions are necessary in order to adapt the pacemaker optimally in terms of its stimulation properties to the individual conditions that pertain.

It is the object of the invention to disclose a pacemaker system with which the control parameters that define the function of the pacemaker can be observed and linked in a manner that on the one hand is optimally appropriate for the desired function of the pacemaker and on the other hand enables wide latitude in varying the parameters.

This object is attained by the novel characteristics of claim 1.

The invention is based on the awareness that with the claimed system, having at least one characteristic field, the parameters can be presented to the physician in a clear three-dimensional perspective reproduction by means of a suitable programming apparatus in viewable form, in which the dependency of one variable on two independent variables at a time are prepared in graph form and can be reproduced in a three-axis coordinate system.

The system according to the invention is universally applicable for arbitrary physiological measured variables and also enables the variables to be linked in various ways, so that further developments and experience can also be taken into account later on by reprogramming. The basic equipment of a suitably prepared pacemaker thus includes a plurality of matrix-like memory regions, which are triggerable as addresses by digitized input variables, and the values present in the addressed memory locations—optionally after weighting—can be linked with other measured values read out of other memories, so that they either form new addresses for a further memory matrix or from a control variable for the pacing. The signal linkages themselves are also to be stored in memories organized in matrix fashion, so that uniform programming is possible by means of an external communication system.

The signal linkages in the manner of characteristic curve fields can be arranged in multiple stages, and the calibration adaptation of signal receivers also is effected by means of such characteristic fields. By means of logical associations and decision fields, predetermined operating ranges can be specified. With memory fields organized three-dimensionally, the operating characteristic curves or operating characteristic fields can be represented in perspective in an external programming and communication apparatus and can be varied by means of personal-computer-based graphics data processing. These characteristic fields can be called up and varied successively (page-turning). In particular fields, the behavior can be statistically monitored over periods of time at predetermined operating points. As a function of the outcome of this monitoring and its frequency, the characteristic fields can be switched, or in other words replaced or varied in their association, so that changes in the lifestyle of a patient or in the clinical picture can be addressed. In the specified operating areas (in terms of the three-dimensional representation, particularly in the heart rate, stroke volume, and exertion diagram), operating characteristic curves that individually prove to be particularly convenient or effective can be selected, and they can also be kept in memory in a varied selection, with data access always taking place to one data set in common.

Despite the complex linkages, monitoring the function of a pacemaker of this kind is simple for the attending physician, because the programming apparatus can individually represent the contents of individual matrix memories depending on the type of characteristic fields they contain, and the memory contents can be monitored for plausibility in terms of individual demands. The input variables are preferably converted so that they form viewable variables, the variation of which in the physiological system can be readily evaluated by the physician. To this end, the extent of physical exertion, the heart rate, the stroke volume and the cardiac output HZV would [sic]. Calibration of individual measured value pickups or the conversion of the measured value ascertained into these variables is then preferably also performed by means of the pertinent characteristic fields, or in two-dimensional calibration curves, so that measured value pickups can be individually calibrated.

At the communication apparatus having the graphic representation functions, the entire programmed system can be apprehended in the form of a block circuit diagram, and the characteristic fields applicable to the various blocks can be made visible on the screen by "turning pages" back and forth through the files. In the memory of the pacemaker itself, only the data and their linkages are resident, while the special form of representation, including operator guidance, is generated for the user in the external control and programming part. The representation techniques selected correspond to the known graphics capabilities of user programs in the personal computer field. Functions can be obtained by selection of the pertinent fields shown on the screen by using a light pen. Characteristic curves can be marked directly on the screen in the form of curve courses. Not only operating characteristic curves but also permissible operating ranges can be selected by outlining their borders.

In another preferred embodiment, the cardiac performance under various exercise conditions is detected and processed in the manner of a histogram (by taking an average of a plurality of events). Memories such as those provided for pickup of the characteristic fields can be used here as well. In this manner the results detected are correspondingly readily available to the physician by using an external control apparatus with graphic terminal functions and the detected data can optionally be used in later operations for controlling the pacemaker. For instance, the physiological parameters that are affected by physical exertion can be "calibrated" by subjecting the patient to a known exertion and recording the associated control variables of the heart.

In the system according to the invention, the signals contained in the memories are processed by means of a microprocessor, and this microprocessor links the data contained in the memories in accordance with a predetermined program. The kind of linkage is also programmable, and additional memory locations are provided for this purpose which are polled by the microprocessor program. The basic program remains identical for all pacemaker types and programs, so that the tailoring to individual patients can be done merely by modifying the software, so that one pacemaker type can be used for all kinds of patients.

The programming can be done without special expertise, purely on the basis of the causal medical relationships. The programming offers the advantage of data variation in realtime operation, that is for the patient, and various data sets can be compared and evaluated in terms of their effect. The data can be input as physical variables, so that plausibility monitoring can be done at any time. Operator guidance and monitoring offers security against improper use, and access controls—such as those typically used with conventional programmable pacemakers—prevent unauthorized persons from changing data. A printer connected to the attached programming system prints out the input data and provides the documentation.

By the linkage by means of characteristic fields, specific control characteristic curves can be defined, which in their linkage are also described by the content of one memory location; in accordance with an advantageous feature of the invention, assorted variant operations can be selected via a plurality of such data words, and the various memories containing these control words are addressable externally. The system is embodied such that this (low-value) addressing can be accomplished using conventional programming means capable of transmitting only a little data at a time. In this way, more-thorough diagnostic programming can be performed in a hospital setting, that is, when the pacemaker is initially implanted, and simple adaptation can also be performed independently at any time. One such possibility is advantageous for instance if the attending physician has initially provided a varied control rhythm on an experimental basis, which might have to be cancelled if the patient has difficulties. In that case, the previous standard program is attainable without particular effort for the patient.

With the characteristic fields, in the linkage of their outputs and inputs, additional simple types of conditions that are not dependent on other parameters can also be programmed. For instance, simple changes can be made by having the patient lie down or stand up, or a determination of physical activity or repose can be made by detecting movements.

In other further developments of the invention, the measured variables picked up by measured variable pickups and characterizing the various physiological parameters are subjected to an analog/digital conversion, and the digital value obtained—at least indirectly—forms the address or an address datum for selection of the output data stored in memory, which may be stored in memory location of a variable memory so that the functional relationship for a set of output variables can be freely defined by varying the memory contents.

The provisions according to the invention provide the advantageous opportunity of linking the input variables of a plurality of measured variable pickups for the same physiological variable to one another. This is done in that the partial addresses for addressing the memory locations of the one memory are generated by combining the digital values formed from the measured values into a common digital value.

It should be added that the tabulation of the functional relationship naturally need not be performed exclusively directly by the association of pairs of values, that is, by storing in memory a variable corresponding to the particular absolute value in the particular memory location; instead, the memory locations may contain instead of the absolute value other data relating to the functional relationship—for example in the form of a measure of increase, or of various differences with respect to a reference value.

Another opportunity for linking two variables relating to the same physiological parameter is provided by subjecting the digitized value to a mathematical averaging operation and subjecting the averaged output values to further processing.

By means of the above-described provisions of tabulated processing of non-linear functional relationships and their linkage, it is possible to process the physiological measured variables derived from the body in a manner that always provides the attending physician a good overview of current signal statuses.

In another preferred embodiment, in addition to the programmable characteristic field memories, a corresponding read-only memory is also provided, which contains empirical values that can be referred to for a great number of patients, so that if the other variable memories have not yet been programmed, limited operation is nevertheless still possible. The switchover to a readout of values stored in memory from these various associated read-only memories can be done by varying a single bit (memory selection bit) so that even in the event of a fault, at least emergency operation is possible.

A further problem in processing a variable derivable in the body is that with this signal linkage, the time-dependent course of input and output variables must often be taken into consideration as well. Although the tabular linkage in the characteristic field as described above does allow taking non-linear relationships into account, it still does not allow ready consideration of chronologically prior or subsequent effects, and so programming non-linear timedependent events would also very greatly limit the clarity of the data display, or might not be performable at all, at affordable cost, because of the complex relationships to be taken into account.

According to the preferred embodiment, a linear timing element is now incorporated in the digital processing branch either before or after a memory addressable in tabular form, this linear timing element simulating one or more timing constants. The type of time constant or time constants, or the corresponding behavior (differential or integral behavior) of a regulating element or a delaying period is programmable by inputting the appropriate parameters. In addition to physical realization by means of analog component elements (active transmission elements with memory elements and resistors, the resistors being variable by means of the programming), digital simulation by a corresponding computer which digitally evaluates the associated transmission function is preferred. In this further development of the invention, the recognition is favorably taken into account in an apparatus that, based on variables additionally derivable in the body, forms an output signal for electrical stimulation of the heart; sufficient precision can also be attained if the time-dependent and the non-linear elements of the transmission functions are processed in a concentrated and separate manner.

Such time constants take into account the fact that quantities of body fluid or other substances contribute to some physiological measured variables derivable in the body, and with such fluids or substances a certain amount of time is needed until they all uniformly assume the physical or chemical measured variable. As an example, the blood temperature or blood oxygen saturation, the pH value of the blood, the systolic intervals, and so forth can be named.

By separating the adjustment of time constants and the other tabular programming, it is possible, in the balancing of the values characterizing the signal processing, to vary those particular values that substantially characterize the particular system in a desired manner by suitable programming or with self-balancing of the system.

In evaluating the body temperature, for instance, for evaluation to obtain a variable characterizing the exertion of the patient, it is advantageous, by processing the measured value for the body temperature (in digital form), to provide a differentiating component first, in order to compensate for the integrating quantity of blood taking part in thermal conduction.

To make the apparatus less vulnerable to fault or malfunction, provisions are made that recognize faults and eliminate them in terms of their effect by switching over to substitute functions.

Two measured value pickups for the blood temperature, one of which is disposed in a peripheral region of the circulatory system and the other of which is provided in the vicinity of the center of the body, furnish different measured values if the physical exertion status of the body changes. In the state of repose, both pickups furnish the same values after some period of time, if they are intact. In other words, monitoring can be performed even with an implanted system if the patient is examined while at rest (and optionally at different levels of exertion) for this purpose. The monitoring of the chronologically stationary behavior of a measured value and thus of a stationary output signal of the measured value transducer makes possible a component for chronological formation of a mean value, so that only those signals that undergo limited chronological fluctuations are emitted as valid. Thus the signals of the two above-mentioned measured value pickups for the blood temperature are redundant in the stationary instance, and they enable conclusions to be drawn as to their function, and also enable mutual calibration.

For calibration, in addition to an ergometrically picked up signal, an additional reference signal that is available is spontaneous action of the heart during operation in which there is no intervention.

A corresponding monitoring of the signals furnished by a measured value pickup is provided by taking into account the fact that the signals established in the body and characterizing physiological variables can vary only at a limited chronological rate. That is, if signal values deviate to a pronounced extent from signals immediately preceding them, then once again this is an indication of a fault function.

It has already been mentioned above that various measured value pickups for the same physiological variable (for instance, the body temperature) may be provided at various locations in the body, to enable greater reliability in their detection. However, in this process other information is also furnished that can affect the timing control. It must first be noted that according to a preferred embodiment of the invention, the signals of such measured value pickups placed at different locations in the circulatory system of the body, in processing by the system shown here, are adapted to one another prior to being united, in a manner suitable for the physiological conditions. By means of a suitable time constant and by means of a relationship—optionally non-linear—that can be stored in memory, a portion of the physical regulating system of the body itself can be simulated.

The calibration can preferably be performed with the system shown here, in such a manner that a pacing rate is first established at stationary exertion, this rate corresponding to the applicable exertion level, and the natural cardiac activity of the patient at earlier times can also be utilized for comparison.

In other advantageous further embodiments of the invention, it is favorable to provide other—optionally external - measured value pickups, which by means of interactive communication of the programming means are connected to the system shown here for information exchange, and in the context of the complete programmability of the system, the linkage of the signal flow routes or the influencing variables are also pre-selectable. In this manner, the behavior of an already-implanted pacemaker can be adapted both to further discoveries by the attending physicians relating to the patient in general, or to the further course of the clinical picture, but additionally progress in medical application of the technology shown here can also be taken into account subsequently as well. The technological realization of the programmability of the linkages is preferably effected in such a manner that an additional memory in the manner of a matrix is provided, in which memory locations are provided for a number of the aforementioned components (tabular memories, time constant memories, linkage modules, mean value formers), and these memory locations hold the addresses of the memory locations in which the input or output data for these modules are to be stored.

The parameters characterizing the electrical stimulation, or pacing, act with variable intensity on the pacing behavior of the pacemaker, and the pacing is preferably influenced such as to adapt cardiac performance to current physical exertion.

A component connected to the output side of the last linkage element serves to adapt the variable that affects pacing of the heart in such a manner that the cardiac performance varied by the pacing (preferably via the pacing rate) is adapted to the parameters detected physiologically in the body only within the particular performance range that the heart of the patient is capable of encompassing.

It is apparent that by means of the system shown here, the entire reaction and control behavior can be programmed and monitored in a viewable manner and in a form accessible to the physician.

Adaptation to particular forms of therapy is possible without difficulty, and for instance in the ischemic heart, the rate ranges in which the heart demonstrates adequate functional capacity can be "dialed" in a purposeful manner by programming, by means of pacing at the appropriate rate in the case of non-spontaneous cardiac activity, so that during operation, the particular "functionally capable operating ranges" of the heart are searched for and located based on the non-linear properties of the system.

Advantageous further developments of the exemplary embodiment are defined by the dependent claims and described in further detail in the ensuing description, in terms of a preferred embodiment of the invention.

BRIEF DESCRIPTION OF THE DRAWINGS

FIG. 5a is a diagram explaining the cooperation of the communication unit with the modules of FIGS. 4 and 4a.

DETAILED DESCRIPTION OF THE PREFERRED EMBODIMENT

In the exemplary embodiment described below of a cardiac pacemaker according to the invention, various components serving to perform signal processing and described as matrix-organized memories or memories containing characteristic fields are used multiply in similar configurations, so that for understanding the invention it will suffice to describe these basic components generally in terms of their function. In the descriptions of the functional cooperation of the apparatus as a whole that are given below in conjunction with the block circuit diagrams, it will accordingly not be necessary to describe the function of these components in detail.

Figure 1:
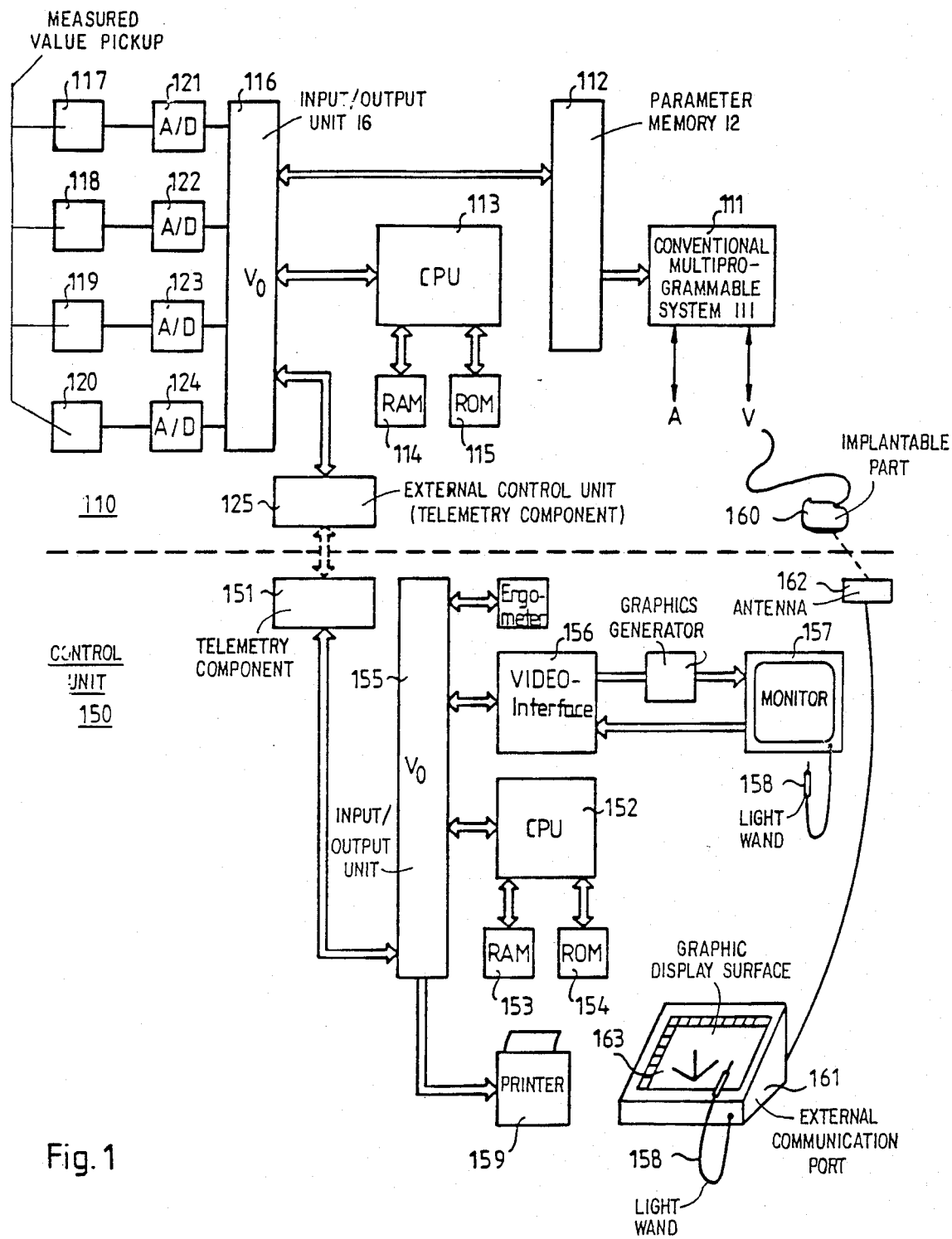
FIG. 1 shows the system structure of an exemplary embodiment of the invention.

In FIG. 1, first, the basic design of a cardiac pacemaker is shown, with means for processing at least one input measured variable for physiological variation, preferably of the heart rate.

On the input side, accordingly, at least one measured value pickup is provided for a measured variable that can be picked up inside or outside the body; this variable can be utilized for physiological control of the pacing rate or—in the case of a demand pacemaker—of the basic heartbeat interval. These variables are of the type that differ from signals electrically derivable in the heart, and they serve only to prevent pacing in competition with spontaneous ventricular actions or to synchronize the pacing pulses, and they relate only to a current heart action. Correspondingly, all the pacing variables can be varied in accordance with the "physiological" input variables for which a relationship for a pacing behavior can be found that is valid over a plurality of heartbeats. These input variables, in turn, are all variables that are relevant to pacing and that are not related to merely one specific cardiac action but rather pertain in general to the pacing behavior. Among them are also the parameters that in pacemakers are "programmable", as well as others to be discovered in future, which improve the pacing behavior—measured in terms of the intended functional capacity of the heart.

Corresponding measured value pickups are known in principle, in the form of temperature-dependent variable resistors for measuring the blood temperature, measuring electrodes for ascertaining impedance cardiographic (electro-plethysmographic) data, photoelectric measured value pickups for ascertaining the blood oxygen saturation by means of a beam of light or light gate, chemical sensors for ascertaining the pH value, or pressure or sound pickups for measured values that have a relationship to mechanical contractions. In particular, the measured variables picked up in the heart itself, and which form a standard for the chamber filling, and thus are already linked with a variable characterizing the cardiac output—and hence the functional capacity of the heart—can advantageously be utilized for varying the pacing parameters (in particular, the heart rate).

Additional physiological measured values can also be obtained from the electrical voltage potentials picked up from the heart, however, such as the Q-T interval, which can also be used to control the heart rate.

In the ensuing description these variables will be called "physiological measured or input variables". A pacemaker that processes a plurality of input signals can accordingly be called a "multi-physiological pacemaker".

The analog output signals of the measured value pickups are each supplied to an analog/digital converter connected to their output side, which converts the input signals into corresponding signals that are processable with the digital memory means or signal processors described. The processing of the data words, each forming a measured value, is effected by means of a microprocessor and its peripheral modules for data storage and data processing.

In the exemplary embodiment shown in FIG. 1, the physical (i.e., hardware) structure of the pacemaker system described below is shown. This is a microprocessor system 110, which is capable of bidirectional communication with an external control unit 125, as a programming unit, by means of telemetry.

The implantable unit contains a conventional multi-programmable system 111, which enters into interaction with the ventricle and/or atrium via one or two electrodes. As an interface with the rest of the pacemaker system, a parameter memory 112 is provided, which at the same time serves as a buffer for data exchange with the conventional pacemaker system. Contained in the parameter memory are, first, those data that are pre-specified to the pacemaker 111 as operating parameters or in other words control variables. These variables form the values of a one- or two-chamber pacemaker that are adjustable by external programming, and the operating mode (from V00 through DDD) is likewise programmable.

Also contained in the memory 112 are operating parameters of the kind that are picked up in the patient's body by further measured value pickups and are derived from "physiological" input variables. In the case of the Q-T intervals, however, they can also be derived via the pacing electrodes themselves.

While the pacemaker system 111 itself thus contains those circuits that prevent competition of pacing events with spontaneous pulses, the microprocessor system encompassing this block serves to define further control variables, preferably the basic rate, and in this sense to expand the system 111. This has the advantage that for using the system 110 in the conventional manner, no additional skills are required beyond those necessary in the use of known multiprogrammable pacemakers.

The pacemaker 111 is capable of operating even without "physiological" picked-up measured variables, the basic pacing rate being predetermined by external programming as in conventional pacemakers. Depending on the technological realization, the necessary signal and data processing for the operation of the pacemaker portion 111 can also be performed by the CPU 113 of the microprocessor.

Associated with the CPU 113 are a random-access memory or RAM 114 and a read-only memory or ROM 115 as well as an input/output unit 116, by means of which the data traffic with the peripheral components 111 and 125 is carried out. It should be noted that with the system shown, signal processing is done in the manner described below, and the memories and data linkages described below are generated by suitable programming, that is, by software, and are already present in the RAM or ROM memory areas. The system is perceived by the user as if it were an apparatus having the described physical structure, which can also be realized by hardware provisions. To avoid having to describe the chronological sequence in the processing of programs in typical data processing structures, which is dictated by the solely serial processing performed by the CPU in a microprocessor system, the description here will be made as if the various memories were generated separately as hardware and were connected to the control and data transmission lines that represent the flow of data in the block diagrams.

Connected to the input/output unit 116 is both the parameter memory 112 and various measured value pickups 117, 118, 119, 120, which via digital/analog converters 121-124 deliver the picked-up signals to the unit 116. The signal pickups were mentioned at the outset above and are disposed in or on the patient's body—in particular on the pacing electrode or on the housing of the pacemaker itself.

The signal processing done by the CPU is serial, and the individual components of the structure to be described below are optionally included in the data exchange in accordance with appropriate interrupt commands, so that the signal processing—adapted to the temporal commands of the signals—is performed in a clocked, quasi-simultaneous manner.

By means of the control unit 150, a data transfer from and to the implanted unit is effected via a telemetry component 151, which communicates with the corresponding telemetry component 125.

The control unit has its own CPU 152, which exchanges data with its own RAM memories 153 or ROM memories 154. An input/output unit 155 is also provided, to which the telemetry unit 151 and a video interface 156 are connected. The video interface is connected to a monitor 157, which in accordance with the program present in the external unit 150 makes it possible to call up data from the implantable system and vary these data. It is particularly significant that the entire operation by the user and the means for graphic display are present in the external unit, including data relating to the general structure of the implantable system. By graphic display of the data obtained and of the findings necessary for programming the internal system, a comfortable mode of operation is provided which provides the operator with information on the operating state of the implantable system at all times. Programming is done by means of a light wand 158, with which data can be selected by contact with the screen. Correspondingly, a pressure-sensitive screen can be used, in which the selection of information is possible by touching the surface of the screen. In accordance with the known techniques of graphic image processing, a selection of screen pages (corresponding to "paging through" a card file), and both during operation and in evaluating the data ascertained during operation, presentation is preferably done in graphic display using internationally understood symbols. The individual function regions of the implantable system can be dialed separately, and a search tree structure leads from those parameter ranges that pertain to the basic functioning of the pacemaker to more-subtle linkages, and this structure is attainable with various access codes to a depth assigned to a particular user. By means of a printer 159, a protocol can be printed out for documentation purposes.

The external form of the components 110 and 150 is also shown in FIG. 1, showing that the implantable part has the dimensions of a standard pacemaker 160, while the external communication part 161 has not only an antenna part 162 that can be placed on the head of the patient but also a graphic display surface 163.

The ensuing description relates to details of the component 116 and especially to the linkage of the "physiological" input variables of the measured value pickups 117-120 as well as to the data linking and the control thereof.

Figure 2:
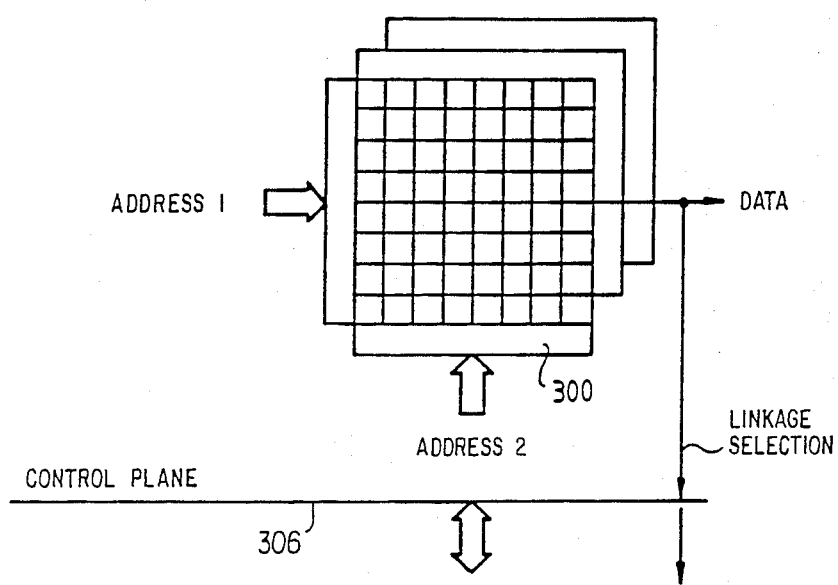
FIG. 2 shows a characteristic field used in the memory region of the exemplary embodiment.

In FIG. 2, the matrix-like memory structure of a characteristic field provided for controlling the system is shown, and the memory locations of the matrix can be addressed by column and line address signals, and the numerical value present at the addressed memory location can be read in or out. Each characteristic field is addressable by means of a common address characteristic, so that on the one hand a simplified addressing is possible in normal operation, but on the other hand a new configuration of the processing and a self-contained reading out or a changing of the contents of one characteristic field can readily be done in connection with the external communication unit.

While in normal operation a linkage of the address inputs and data inputs or outputs is done in accordance with a predetermined linking plan, where in preceding characteristic field memories, data read out by addressing serve to address successive characteristic field memories, these data can also contain information which relate to the linkage of the data with successive characteristic fields themselves, either in terms of the direction of the linkage or in terms of the operations to be performed (logical or mathematical) in the linkage. The corresponding data contents differ from one another in additional attributes, which can be distinguished in suitable subsequent data discriminators (not shown). During the external communication, by means of the common address characteristic of each characteristic field memory, direct access to the contents of the particular total memory region is possible for reading data in and out or changing data. The characteristic field data for the data processing preferably have access addresses, which can be called up similarly to those of auxiliary memories, and which contain solely linkage, selection or other auxiliary information such as data sets that can be read out from the communication unit with graphic data or specifications for the particular pacemaker type.

Figure 3:
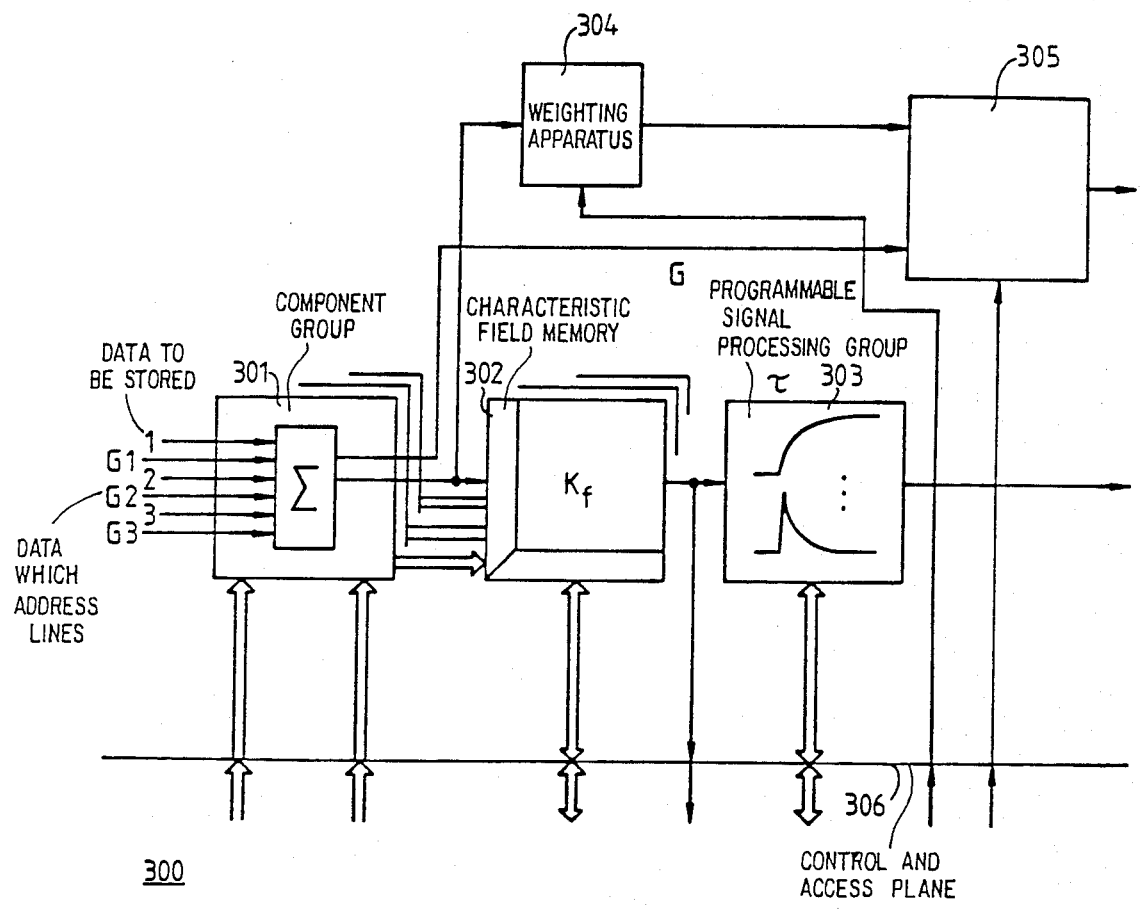
FIG. 3 shows the elements existing in a signal processing module, including a characteristic graph according to FIG. 2.

This direct access is represented in FIGS. 2 and 3 in the lower part of each of the drawings by the control and access plane 306. Accordingly, a data field may be not only a module of the signal processing, in the sense of linking input and output signals but may also be a memory, the information in which form for determining the sequence in terms of combining together input and output data of various characteristic field modules.

The memory unit shown in FIG. 2 need not—as shown—in this form embody a physical or hardware-type unit in the memory region of the system. The pertinent structure can also be generated purely by software.

The memory unit of FIG. 2—which here is also synonymously called the "characteristic field memory" or "memory matrix"—forms a part of a "cell" shown in FIG. 3 as a signal processing module, in which the memory unit is also surrounded by auxiliary components, which are favorably provided in a modular structure in each charatristic field and which are linked along with them in the network formation, so that only the inputs and outputs of this cell appear as interfaces. Modules not needed in a particular application are each rendered inactive by the loading of appropriate control parameters in the auxiliary memory (as will be described hereinafter).

The combining of the signals of various measured value pickups is effected in a block 301, taking into account the weighting signal assigned to each signal of each measured value pickup. The block 301 also at the same time forms a switch component, which via the access plane 306 selects various signals as input (that is, address) signals and depending on the "switch position" (influenced via the selection information of the control plane 306) links various signals by means of the following characteristic field for the variable addressing of the output of signals from the following characteristic field memory 302, in the form of digitized amplitude data. The selected input signals each form partial address signals, which taken as a whole encompass the memory range of the following characteristic field. By means of linking data to be supplied separately to the block 301, the input data can not only be switched but also (individually or in common) subjected to logical or mathematical operations; that is, data can be selected, shifted or in some other way "processed". In particular, operating ranges or operating characteristic curves can be selected in this way, and the selection data, which characterize authorized address regions, are stored in a suitable characteristic field.

With parallel addressing of the memories containing the signal data and the selection data, and linking via block 301, the selection data (for example by means of an AND linkage called up via the control plane 306) characterize only signal data that have a data value deviating from "zero" as authorized addresses. The selectable address range can thus be restricted or affected in some other way arbitrarily. Preferably, a limited number of linkage operations that are to be used often are held in reserve for this purpose such that they can be called up directly via the control plane. Input variables can also be subjected to more-complex operations by means of a correspondingly programmed characteristic field memory, which authorizes any evaluation of input signals by means of a corresponding specification of output signal values as data values in the pertinent memory locations addressed by combination of the input signals. On the other hand, input signals can also be subjected exclusively to illogical linkage in the block 301, with the following characteristic field either being "bridged" in terms of data processing by a corresponding control signal (not shown), or it is rendered ineffective by the pertinent characteristic field by storing the addresses in the memory locations, so that the input signals appear directly once again at the output of block 302.

The control plane 306 itself can—as also shown hereinafter, referring to FIGS. 3 and 4a—be reached by output signals of the characteristic field memory 302, so that as a function of signals contained in characteristic fields, the signal linkage can be influenced via the blocks 301. A data set contained in a corresponding memory 302 accordingly includes not only an instruction as to whether it is signal, selection, or linkage or other auxiliary information, but also in the case of selection information the designations of the pertinent characteristic field cells that form the output and input for the signal to be processed. In the case of linkage information, the agreed-upon designation of a logical or mathematical operation is also included.

Additionally, as a function of data addressed in characteristic fields, a plurality of data linkages can also be affected in the overall structure of the system. These are stored in fact by means of linkage memories—as will be described hereinafter. If such a linkage memory is called up, by means of a signal contained in a memory location, the system structure changes more or less fundamentally. In this manner, the cardiac pacemaker described is "self-teaching" in such a manner that the configuration of the processing can be predominantly automatically adapted in terms of the measured value selection in processing to the input signals found and to their changes. Such changes are in particular the following: the shutoff of malfunctioning measured value pickups, and in this connection in particular the transition from operation determined by a plurality of physiological measured value pickups to the mode of operation that is influenced by one such pickup, or by no such pickups. While two measured value pickups for the same variable can often be operated in differential operation, a single remaining pickup can often—given a suitably increased error probability—contribute effectively to control as well.

Together with the data signals, evaluation numbers are also carried in the processing, which in an evaluated combination contain a conclusion as to the value of an input signal in terms of its expected reliability. The evaluated combination is preferably performed with standardized input signals. It links input signals containing identical information to form one combined output signal, which is done in accordance with mathematical laws for the formation of mean values of measured values having weighting. This mean value formation can be effected either by digital processing, via calculation in accordance with a relationship expressed in a formula, or by means of a table storable in memory in the form of the characteristic field memory. To ascertain the weight of the pertinent input signal, additional evaluation of the pertinent signal in terms of inherent faults are expressed by unexpected fluctuations or superimposed amplitudes. The corresponding malfunction recognition circuits correspond to circuits such as those already used for the elimination of faulty input signals in medical electronics.

Accordingly, digitized data of various types are supplied to the component groups 301. In detail, the data of one input plane each are combined following a linkage that can be predetermined via the external programming access plane 306. The input signals serve to address the lines of the characteristic field memory 302, and the data $G_1$–$G_3$ serve to address the lines, while the data 1–3 relate to the data contents—that is, the data to be written into the individual addressed memory locations.

Via the external control (access or programming) plane, the type of linkage in the memory 301 can be predetermined, and various mathematical linkages (summation, multiplication) or logical linkages can be selected, so that the data can be added, multiplied or otherwise transferred in accordance with a logical condition; the logical conditions may comprise not only AND, AND/OR or other known linkages performable by logical gates, including "greater than", "less than" or "equal to" relationships. It can also be predetermined that while satisfying the predetermined condition a particular fixed logical value will be output. The component group 301 accordingly allows the processing of signals with either a fixed logical level or with a variable level in digital representation.

The number of planes of the component element 301 increases accordingly if the characteristic field memory 302 is embodied multidimensionally, as indicated by the perspective layering in FIG. 3. For each dimension, an additional addressing plane is required. The illustration in FIG. 3 is accordingly more symbolic in form. Any other suitable embodiment of the actual memories is also possible.

Following the circuit 302 is a programmable signal processing component group 303, which enables a time-dependent linear processing of the signal value, while in the component group 302 a non-linear, tabulatable relationship between the input and output variable is present in the form of a characteristic graph. The two component groups 302 and 303 are to be influenced by external programming means via the control plane 306, and preferably the coefficients of a linear differential equation determining the chronological transfer behavior (in a similarly matrix-like arrangement corresponding to the other data component groups) are preferably capable of being fed into the component group 303. The chronological processing is done by means of the internal microprocessor in accordance with such systems that by digitally adjustable parameters enable the digital simulation of linear physical systems. By the separation of non-linear and linear system components of the signal processing, a simple system structure is obtained with simple adaptability, and the system is uncomplicatably adjustable externally.

The signal processing portion 303 may also effect a signal delay in such a manner that by means of a certain parameter, a predetermined signal delay is predetermined (by the designation of the corresponding number of clock signals of a system clock), and thereupon the output signals appear delayed at the output, as compared with the input, only by the indicated number of clock signals, the delay being in accordance with the set number in the manner of a digital delay line (shift register). The representations shown in block 303 provide examples of a possible transfer behavior, which is described by the characteristic values of the pertinent linear differential equations.

The component groups 304 and 305 generate an identification for the reliability of the signal emitted by the component 300, which is supplied to the input of the following corresponding component, so that in each state a standard for the reliability is provided, which can be taken into account in the ensuing combination. Faulty signals can be eliminated in this manner, so that in the ensuing processing, access is made instead to other, error-free signals.

Thus it can be ascertained whether the pertinent input is associated with faulty signals. An indication of this occurs if with measured values which are inherently subject to a slow change (blood temperature, etc.), signals arrive for processing that have an abruptly changing character. Furthermore, one criterion is that in the comparison of two or more signals which under certain conditions exhibit an identical course of change, deviations from this identical course occur. An important fact for processing with the pacemaker described is that in the form of an additional datum of at least one bit, an identification relating to the reliability of the corresponding measured value—or in accordance with the time-dependent processing in a component 303—is added to the digital input signals, for a linkage of measured values.

In the simple case for error recognition, the weighting apparatus 304 includes a mean value former and a comparator, to which the input signal from the component group 301 is supplied directly and the output signal of the error recognition is also supplied, and if the input signal deviates beyond a predetermined amount the output signal of the weighting apparatus 304 indicates that the input signals possibly have only a reduced reliability, so that the weighting in the evaluation is to be decreased accordingly. The signal G combines the weighting signals of previous stages, which stages have already performed respective corresponding evaluations. In the component group 305, the signal G is added to the output signal of the stage 304, and the evaluated combination is made available to the stage 300 as an output signal. The component groups 304 and 305 can likewise be switched via the control plane 306, as well as in accordance with signal data and by means of external programming.

The "cells" containing characteristic fields may contain variant kinds of information. For example, they form read-only memories even without linkage of their data contents with other cells, and they are addressable by means of physiological measured values or output signals of other characteristic value memories. In this manner, regions that are run through by the (address-forming) input signals can be particularly identified for subsequent stages or for external communication with graphic representation. Authorized operating ranges or emphasized ranges, or logical linkages on the other hand, can be predetermined. If the memory contents, as output signals, are not intended for subsequent memory cells for addressing or as data signals, such characteristic fields can also serve merely for the information of the user or for controlling the communication system, in order to emphasize particular operating ranges for the external communication in the graphics used there.

Figure 4:
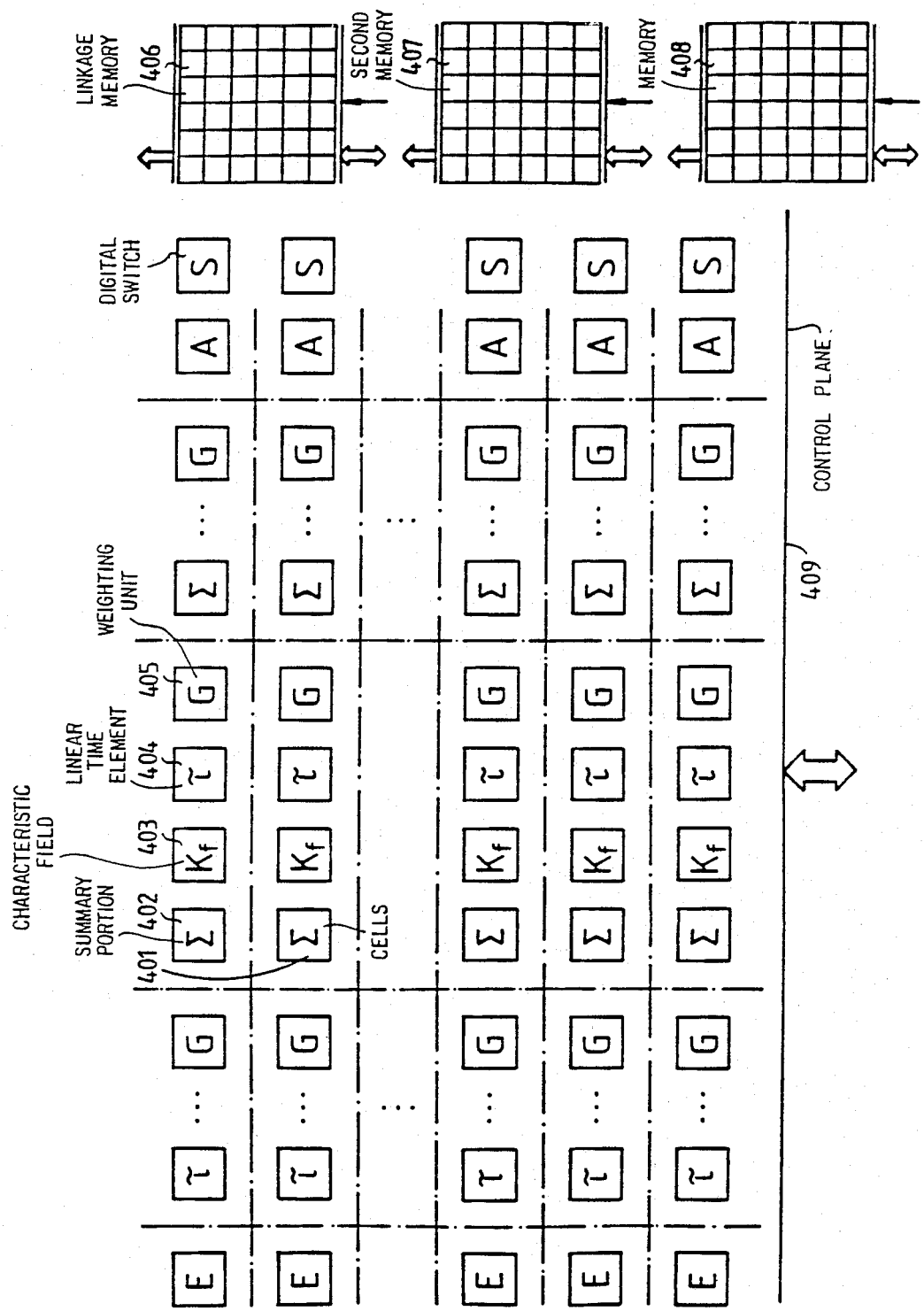
FIG. 4 shows an arrangement of signal processing modules for programmable linkage.

In FIG. 4, the arrangement of the above-described component groups in a matrix-like structure is shown, in a manner that is the basis for the addressing of the individual component groups in the context of their linkage in a linkage memory 406. For the association of the selection, they can also be presented correspondingly graphically. A function group addressable by means of line and column numbers includes the function elements, of a cell selectable as such by addressing, comprising a summing portion 402, characteristic field 403, linear time element 404 and weighting unit 405 (corresponding to the illustration in FIG. 3). These function groups are repeated in an arbitrary line and column grid, and by means of two memory ranges organized in matrix fashion on the one hand for each functional component group in terms of its inputs, the "map square" of that particular component group the output signals of which are supplied to this component group can be input. Since the summing unit 402 has a plurality of inputs, a plurality of columns and address identifications can be provided for each component group.

Additionally, the output signal data can be associated with the following cells, as described above. In the outermost column on the right of the memory 406 receiving the linkage information, for example, the input variables of the pacemaker system are each assigned to one memory element of one line, so that by means of the corresponding input it can be determined whether the output signals of which component group should form the pertinent parameters. The first memory 406 contains the signal linkages valid in normal operation—in a manner programmable by the external communication portion.

In a second memory 407 organized in matrix fashion, the system structure for an alternative operating state, such as can be called up by the signal data themselves via the control plane 306 (409), is shown—once again in column and line association.

Figure 4A:
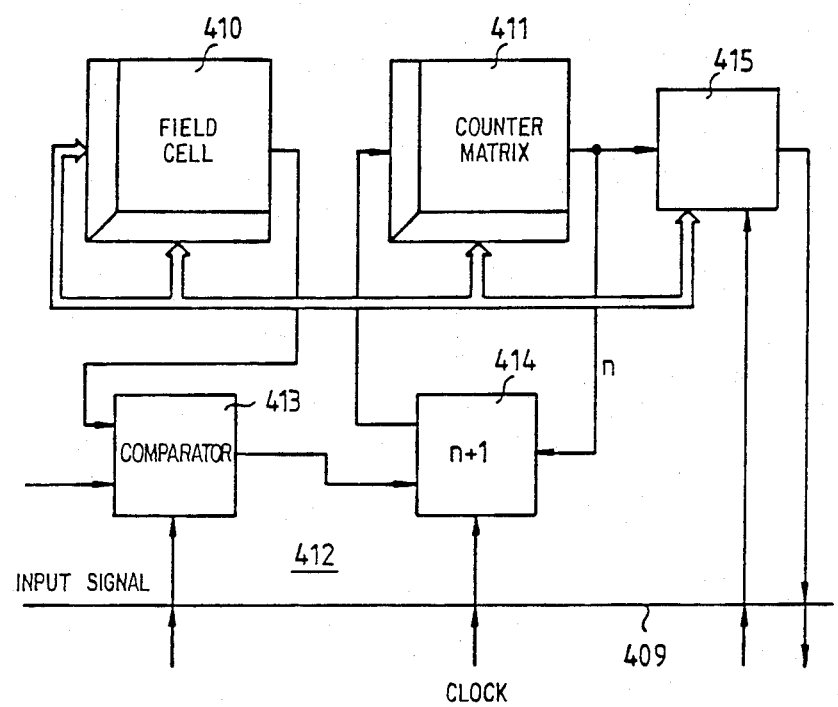
FIG. 4a shows an auxiliary module for signal storage and linkage in connection with the arrangements of FIGS. 3 and 4.

In FIG. 4a, it is shown how by linking two characteristic field cells 410 and 411 (corresponding to the cells 401 in FIG. 4) and one counter cell 414, a histogram memory is formed, can, which upon later being read out provides information as to behavior of the pacemaker system.

The cell 410 here forms a (programmable) reference field, in the memory locations of which, which are addressable by means of output signals of preceding cells or by input signals, values are stored that serve as reference variables in comparison operations. In a counter matrix 411, counter states are stored in the individual memory locations, which once again are organized in matrix fashion, the counter states representing the appearance of particular events—in the normal case, the exceeding of or failure to attain the corresponding reference value contained in the cell 410. The memory cells 410 and 411 are addressed in parallel for this purpose. The input signal which is to be compared with the values stored in the reference cell 410 is supplied to a comparator 413, which compares it with the particularly addressed signal in the reference cell 410 in accordance with an externally predeterminable condition. If the condition is met, then by the single occurrence of this state (controlled by a clock signal), the value present in the addressed position after the output of the counting memory is raised by one and read in again. In this manner, a characteristic field to be read out later is produced, which in the graphic representation indicates the frequency with which predetermined operating values are attained.

The possibility of varying the operating behavior of the pacemaker taking into account the frequency with which predetermined operating values are adhered to as well is also provided. To this end, preferably the contents of the counter characteristic field 411 of FIG. 4a is supplied to a block 300 shown in FIG. 3 as an input variable, and the operating behavior is varied in accordance with corresponding logical decisions by means of a corresponding characteristic field. To this end, the characteristic field matrix addressed on the basis of the counter state (behavior in the past) is followed by a further characteristic field memory for the call up of different characteristic fields, which vary existing linkages (linkage memory 406 in FIG. 4, or affect the parameter memory (112 in FIG. 1) or correspondingly switch over or replace characteristic fields serving as read-only memories. To this end, it is favorable if the parameter memory 112 which influences the conventional behavior of the pacemaker is likewise designed in accordance with the characteristic fields that monitor the physiological control. In this manner, it is also possible to program the conventional portion in accordance with the processing of the physiological parameters.

"Physiological" measured variables, which are ascertained in the conventional portion of the pacemaker, such as the Q-T interval or a spontaneous frequency occurring at particular states of exertion, can thus be transferred into the remaining system via the parameter memory 112 as an interface. This interface is also suitable for the transfer in ascertaining physiological variables via the electrodes or other measured value pickups provided in the conventional region of the pacemaker.

Via a corresponding control of the control plane 306, a switching element which as a function of the output signal of block 411 emits a signal to the control plane, which signal influences a linkage matrix 406 which in turn again triggers the block 301 (in FIG. 3), can be connected to the output side of the block 411 (or any other component group). In this way, as a function of the previous behavior—optionally also to be averaged over predetermined time segments—the future behavior can be influenced. Characteristic fields can be switched over, or in other words exchanged, evaluated differently or changed in their linkage with preceding and subsequent characteristic fields. How these changes should be made is stored in the characteristic fields involved which store the linkages. The system is thus likewise "self-teaching", and a change in the configuration is not done until there is a certain frequency of events. A standard for the change of the system behavior is faults of a predetermined frequency or intensity, or the non-occurrence of predetermined operating states, which from the standpoint of therapy necessitate a certain pacemaker configuration, so that the pacing can always be done in the simplest kind of operation—and the one easiest for the physician to monitor. Thus the physician is also capable of using the memory for monitoring success of the programming he has performed.

Now that the basic component groups have been described, the cooperation of these component groups will be described in further detail referring to the block circuit diagram of FIG. 5. Particularly important for the operation of the system is the fact that the signal variables are linked in accordance with their physical or physiological significance. In accordance with a calibration table (characteristic field) connected to the output of the relevant measured value pickup, a conversion into a variable adapted to the current performance deficit of the heart is now effected in a further processing cell. A differentiating component is assigned to the blood temperature, since a rise in temperature always takes place with a delay as compared with the current exertion level. An increase in exertion beyond a predetermined value is limited in time (the contents of the counter matrix 411 in FIG. 4a is raised by means of a system clock serving as a time clock). When a predetermined duration of time is exceeded, the emitted exertion variable is lowered by means of a corresponding switchover of the pertinent characteristic field via the control plane, until the temperature again attains a lower output value. In this manner, in a fever condition a permanent increase in the heart rate is avoided.

The physiological variables picked up in the body are each linked on corresponding "linkage planes" with the further identical signals, so that a physically correct further processing takes place. Between two linkage stages (if necessary), an adaptation of the temporal and amplitude behavior of the signal to be processed and linked is performed, so that the pertinent signal is adapted at the particular linkage location with a further physiological variable, which is of significance in controlling cardiac activity. The advantage is thus obtained that the system can operate parallel to the signals taking their course in the body and calling up a variation of the cardiac activity and parallel to the endogeneous regulation processes, and in the various linkage stages the particular pertinent physiological signals are likewise ascertained at the pertinent stage by additional measured value pickups and are usable either as monitoring signals or are incorporated in accordance with their value into the further signal processing. A separate characteristic field memory is provided for the "calibration" of each of the measured value pickups.

A further factor is that signals which on the one hand are standard for the performance required and on the other hand are jointly characterizing for the cardiac output itself, as well as variables that are only briefly available (monitoring measurement of physical exertion by means of an ergometer for the sake of calibrating measured value pickups) are likewise fed in in a system-correct manner and enable a conclusion to be made as to the processing capability of the preceding stages, or permit correct setting of the corresponding processing parameters (components 302 and 303). Furthermore, by feedback of a variable that enables drawing a conclusion as to the cardiac performance capability, the signal processing can also be influenced. This feedback is done in such a manner that the physiological measured values in the processing are combined and converted in such a manner that they form a standard for the instantaneous requirement of the cardiac output. A criterion for the actual cardiac output derived from the heart is utilized as a comparison criterion, this cardiac output being taken into consideration as feedback in the selection of the pacing rate in the context of the table. In a preferred embodiment, the table establishing the pacing parameters is updated based on the cardiac output actually established with the pacing using the pertinent parameters. In the case of input addresses that require a particular cardiac performance, the particular pacing parameter, or signal values that lead to the necessary pacing parameters, are entered.

For the linkage of signals in the form of digital characteristic field, the following basic principles—depending on the applications mentioned—arise:

1. Pure control functions are formed by simple linkage of input measured variables of address variables and by the pacing parameters as stored values.

2. Regulation functions are realized in a corresponding manner, with measured input variables being converted by corresponding characteristic fields into a variable that is representative for the physical exertion, in accordance with the required cardiac output. This variable addresses the characteristic field together with a variable representative of the current stroke volume, and the then necessary heart rate can be read out of the individual memory locations. In particular, instead of the various absolute values, the particular deviation from a predetermined set-point value is usable as a signal value, and the ensuing processing then likewise relates to the corresponding deviations. In the case of measured variables which follow the actual physical reference value with a temporal delay, a compensation is preferably provided where the pertinent measured variable is present in the most unadulterated possible form. The temporal delay in the rise in temperature of the blood during physical exertion is compensated for by differentiating component (303 in FIG. 3), so that the rate change begins more quickly.

3. The calibration of a measured variable dependent in particular on exertion is effected by providing that in the calibration period, the value expected (and optionally ascertained by a different measuring method) is respectively written into the memory location addressed by the current measured variable. In particular, to this end the exertion ascertained externally by means of an ergometer is written into a memory to be addressed by means of the measured variable or variables characterizing the exertion, in each case in form of a value. This value in turn, during the subsequent operating state, addresses the corresponding rate in a characteristic field, and this rate is selected such that (in particular in the case of combined addressing with a measured value representative of the current stroke volume) the product of the stroke volume and the rate, as the cardiac output, corresponds to and is followed up with the ascertained current exertion variable.

4. The error control is ascertained by comparison of two (or more) variables. The pertinent characteristic field effects a shutoff of one or all values, in the case of deviations that are greater than a predetermined extent. In the addressing of memory locations, correspondingly, with three comparison signals the particular signal that deviates substantially from two others can be excluded from further processing. To do this, a characteristic field is needed which is addressed by address signals in which all three address components are combined. Three different signals acting as shutoff commands are contained in the various memories addressed by the unauthorized signal combinations, and in the event of a deviating signal preclude this signal from further processing, and in the case of two deviations preclude all three signals from further processing. Furthermore, (optionally in accordance with further signals), expectation values can be predetermined, which permit further processing of the input signals (by logical association in a corresponding characteristic field memory) only whenever the input signal is within a predetermined expectation interval.

5. In the control plane, a selected operating characteristic curve is predeterminable (for example by external communication), in such a manner that in an additional characteristic field (addressable by only one input variable) the value is firmly associated as memory contents with the other variable. This can be done for example by means of a calibration process (as indicated above). The second characteristic field is then merely "one-dimensional". In a perspective (graphic) representation of a two-dimensional characteristic field, the points on the operating characteristic curve can also be represented such that they are graphically emphasized, by superimposing the one-dimensional characteristic field. With one operating field, a corresponding region of input signals in a characteristic field is declared allowable, by means of corresponding memory contents and subsequent logical linkages, and delivered for further processing.

Figure 5:
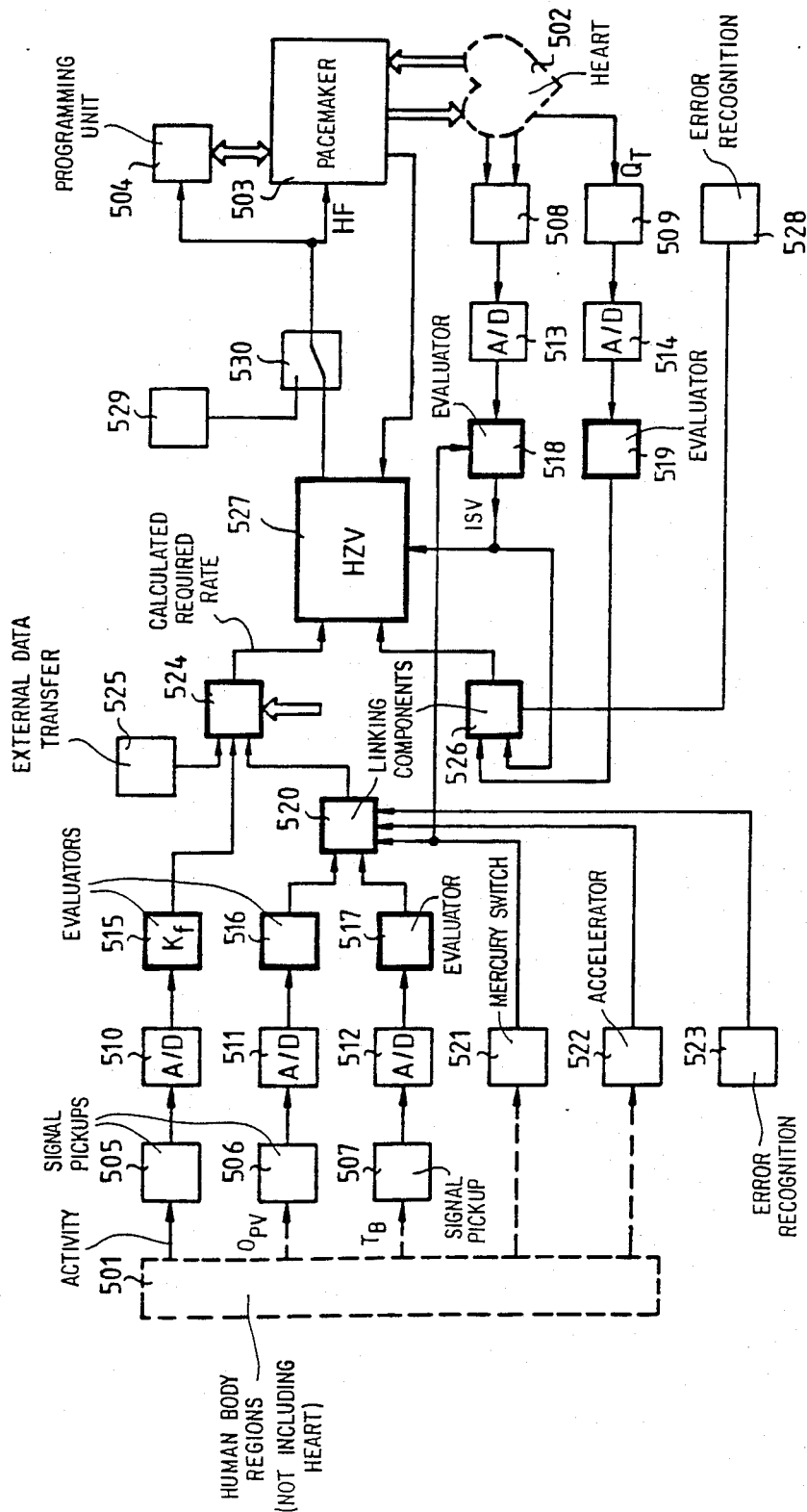
FIG. 5 is a block diagram for a cardiac pacemaker realized according to the invention with the aforementioned modules.

In FIG. 5, a pacemaker system as it is presented to the attending physician on the screen of its control unit is shown in block form. At the same time it represents the basis for the functional description of a pacemaker system of a kind that can also be generated in a conventional manner—for instance by means of hardware. FIG. 5 shows the implantable portion, and the pertinent arrangement is naturally not restricted to implantable systems but is also applicable to external pacemakers correspondingly. The block 501 shown in dashed lines characterizes the regions of the human body located outside the heart, from which physiological measured variables are derived that pertain to the function of the pacemaker, while the heart 502 enters into interaction with the system via the pacing electrodes and measured value pickups emplaced in the heart.

A conventional pacemaker 503 is capable of functioning autonomously and is optionally multiprogrammable via a programming unit 504. (In a system shown according to FIG. 1, which represents the real linkages, the programming is done by means of the unitary control unit by means of the parameter memory 112.)

In the system presented graphically to the physician as shown in FIG. 5, the programming is done with a block 504, which can be called up on the control unit in the form of a page and contains the conventionally programmable parameters in the usual designations. Selectively, different types of pacemakers can be implemented completely here. The translation of the real parameters set in the implantable system into a conventional system is done in the external control portion, and a selector switch is provided which permits different kinds of implantations.

The blocks outlined in solid lines are component groups according to FIG. 4, which contain the function elements of FIGS. 2 and 3 and are logically connected in the manner shown by means of the linkage matrix indicated in FIG. 4. The exemplary embodiment according to FIG. 5 shows exemplary types of linkages in a preferred embodiment, the operating mode of which will be described in further detail hereinafter. It is apparent that the output signals of various analog measured value pickups 505–509 in the block diagram are linkable in different groups in the course of the signal processing. Previously, a conversion of the analog input variables was done by means of analog/digital converters 510–514. The output variables of the converters are supplied respectively to evaluation component groups 515–519, in which an individual, or in other words programmable, adaptation takes place. This adaptation, by corresponding programming of the characteristic field shown previously, includes the elimination of non-linearities of the measured value pickups, enables the programming in of time-dependent changes of the transfer characteristic and of weighting factors. Thus the transfer behavior of a measured value pickup can be changed by means of the characteristic field programming.

While the measured value pickups 506 ascertain the partial pressure $O_{RV}$ of oxygen in the right ventricle or the respiration rate, the measured value pickup 507 serves to ascertain the blood temperature $T_B$, preferably in the vena cava. While the partial pressure of oxygen or the respiration rate is a good standard for the instantaneous oxygen deficit—presuming a suitable calibration of the corresponding characteristic field—the blood temperature has an integrating character and rises or falls only after a certain time delay. In order in the component 520 following and identical to the blocks 516, 517, which component 520 links the output variables of the precediang blocks with pre-programmed weighting (with an exertion variable obtained as an agreeing reference base), inside the component 517 the time constant is provided by corresponding programming with a differentiating characteristic, so that preferably the differential changes of the blood temperature as a standard for a state of activity or repose are linked with the output variable of the block 516.

The superposition can be done either by weighted sum formation, linearly, or by means of a characteristic field, and in the case of a two dimensional characteristic field one input variable each addresses one coordinate axis. The linkage in the component 520 is also dependent on sensors 521-523 emitting a number of digital output signals, which sensors—as described above referring to FIG. 2—effect switchovers of the characteristic field present in the block 520. Thus a mercury switch 521, which is implanted along with the pacemaker housing, recognizes the instantaneous position of the patient (lying down, standing up) and thereby furnishes an additional possibility for evaluating the exertion of the patient. A digital activity sensor 522 furthermore recognizes, by the appearance of accelerations and decelerations beyond a predetermined threshold value, whether the patient at the time is generally at rest or in motion and switches the characteristic field located in block 520 over accordingly. The control of the measured value processing is affected by means of a common system clock, to assure synchronism.

A digitally operating error recognition means ascertains whether an exertion variable at the time can just then not be ascertained. For instance, if the respiration rate is picked up by means of a microphone, then by means of an additional microphone present in the error recognition unit 523, loud noises originating in coughing by the patient or the like are recognized and utilized for blanking out the measured values of the pickup 506, which could be done by switchover of the corresponding characteristic field, or also be reducing the weighting factor by connection with the block 516.

An additional measured value pickup 505 forms a recognition for the activity of the patient with an analog output signal. In accordance with the component 522, the acceleration and delays are ascertained in terms of amplitude and frequency and processed further via the component groups 510 and 515.

While in the component group 520 the exertion variables ascertained in the circulatory system were combined, the block 524 serves to unite the output variable of the block 520 with a signal designating the actual physical activity. The output signal of the block 524 thus indicates the cardiac output (HZV) requirement. The output signals of the blocks 515 and 520 are to some extent redundant and can be put in relation to one another in the subsequent characteristic field in order to increase the reliability.

Of particular significance is an additional transfer component 525, which is included in the telemetry system of FIG. 1. Via this component group, external exertion data ascertained by means of an ergometer can be fed into the block 524, and by means of external programming both the output variable of block 515 and that of block 520 can be set in relation to the instantaneous load. By insertion of the current exertion data into the memory locations of the characteristic field in block 525, which locations are addressed by the means of the output signals of block 515 or 520, the other signals characterizing the HZV requirement can be monitored or calibrated, so that the reliability of the system can be increased or a regulation brought about. By the transfer and calibration of the exertion signal available outside the body with the corresponding intracorporeally obtained signal, a possibility for calibration or a linkage for regulation can be obtained.

Two further measured value pickups 508 and 509 ascertain signals which likewise relate to the cardiac output. In the illustration in FIG. 5, the measured value pickup 508 for the stroke volume represents (via the systolic intervals as a pressure pickup or microphone or by means of impedance cardiography or a combination of the two methods) a standard for the volume adaptation of the heart as a reaction to a predetermined physical exertion. The further measured value pickup 509 for the Q-T interval ascertains a standard for the current rate requirement from the signals picked up in the heart at the pacing pulses, likewise by means of a corresponding characteristic field. Following a corresponding analog/digital conversion in conversion blocks 513 and 514 and an optional non-linear distortion of the transfer behavior are blocks 518 and 519 containing characteristic field groups, the combination of the variables determining the rate takes place in a block 526.

The linkage of the variables characterizing an HZV requirement is effected in block 527, and depending on the programming of block 527 various linkages can be selected:

The output variables of blocks 524 and 526 can be superimposed on one another and control the heart rate directly (as the basic rate of the demand pacemaker 503). This control can be performed taking into account the instantaneous stroke volume ISV (arrow from block 518 to 527), so that all the variables that have an influence on the heart rate are processed in combined form, and a favorable cardiac output for the instantaneous rate based on the ascertained variables is established. The additional evaluation of the stroke volume in block 527 can be done with a different weighting than that fed into block 526 as a trend for the rate to be adhered to, so that in particular, regulation fluctuations can be avoided here. If a great number of variables that must be ascertained in a stable fashion are present, then optionally the stroke volume can be left out entirely from the processing in block 526. The same applies to the variable $Q_T$.

In a corresponding manner, the pacemaker can also be used in regulated operation, where only the linkage in component 527 needs to be converted. To this end, the HZV requirement in the characteristic field of block 527 is calibrated with the product of the stroke volume and the instantaneous rate, the rate being raised or lowered until the product of the stroke volume and the stroke rate corresponds to the cardiac output predetermined by the block 524. It is apparent that by means of different linkages, various control or regulating mechanisms can be realized, and in particular within the characteristic field the rate can be varied incrementally by means of a search strategy in such a manner that the largest possible cardiac output is attained.

An additional error recognition means 528 shuts off the signals picked up in the heart if faults are ascertained there, and the error criteria correspond to those that in demand pacemakers prevent control of the pacemaker by the heart.

An arrow from the output of block 527 and pointing toward the parameter memory 504 indicates that the programmed parameters of the pacemaker undergo variation. Among these is in particular an expansion of the programmed time variables, such as refractory or blanking times with decreasing frequency. This relationship can be related generally to the time control of the pacemaker. The programmable variation in block 504 is effected preferably by means of a characteristic field stored in memory there, the memory of which, containing the programmed operating values of the pacemaker, is addressed by means of a variable derived from the frequency.

The pacemaker 503 is in particular a single-chamber pacemaker for ventricular stimulation, because in this way it is unnecessary to place an additional electrode in the atrium. The measured value pickup for further physiological variables are disposed in the pacemaker housing or in the ventricle electrode, so that the implantation technique does not differ from the conventional pacemaker, or is even simplified as compared with AV pacemakers.

Figure 5A:
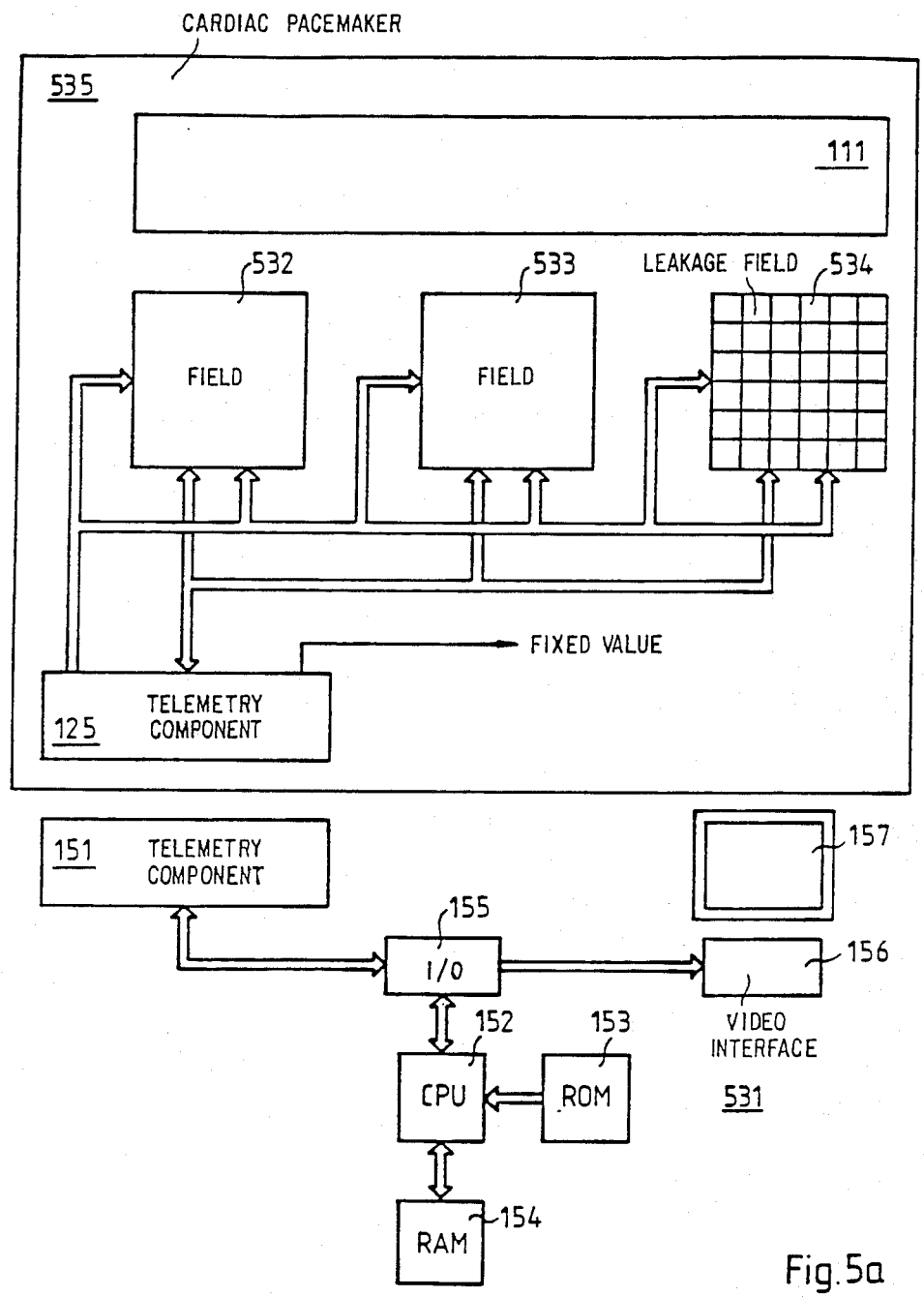

FIG. 5a shows how by means of the external communication unit the individual characteristic fields 532–534 are addressed in the corresponding cells—as described above—and data located there are read out or new data are read in. The addressing is effected independently of the other operation of the cardiac pacemaker 535, which is determined by nonphysiological data, and during the programming of the physiological portion this control is rendered inactive (fixed-value signal). The basic pacing rate and the other physiologically determined operating parameters are fixed during the programming to a value corresponding to the resting state of the patient.

As a special feature it is also provided that by means of the configuration data (characteristic field 534) contained in the pacemaker, which data define the data linkage of the characteristic fields, a graphic representation is called up, which corresponds to this configuration. The individual characteristic fields are represented as blocks on a screen or LCD screen and can be called for programming by dialing with a light wand or by means of pressure in the case of a touch-sensitive display. The particular characteristic field called up, or the corresponding component, then appears enlarged on the screen, so that the data fields marked with a cursor can be changed. To facilitate programming, arbitrary individual structures of the linkage diagram can be called up and varied using the so-called "windows" technique. Here not only data sets but also, depending on the access authorization of the communication portion, configurations of the processing (input and output linkages) can be changed as well, so that the system is extremely flexible and can be tailored to an individual patient in accordance with the empirical values obtained. For calling up the graphic representation of the screen configuration, either the data of the configuration characteristic field are used for direct addressing of a corresponding memory region, or a corresponding block circuit diagram is synthesized based on the pertinent linkage information, using CAD techniques.

It is particularly advantageous here that the communication system shown can be incorporated in a standard type of data processing system (PC or the like), and the communication interface with the pacemaker is provided by an additional assembled circuit board that can be inserted into the PC, which is furnished along with the associated software that contains the above-mentioned functions in programmed fashion, so that the communication portion in an existing PC entails only slight additional cost. Nevertheless—depending on the existing expansion of the PC—a very great processing capacity is available, which enables the simultaneous call-up and representation of even complex illustrations, and the operator guidance provides the user with instructions and warnings for the configuration programming of the system. Via a printer, a protocol relating to the programming process is prepared, which documents the set operating state of the pacemaker. The programmed data inputs for the configuration can simultaneously be stored in a central memory, so that the operating parameters of the particular pacemaker can preferably also be called up via external data communication options and in emergency cases be available to any physician. The programming portion is designed in particular as a communication terminal, so that complex software that also relates to operator guidance and to the configuration of the pacemaker is centrally stored in memory and transferred to the particular communication terminal. In this way it is assured that in programming, the latest software is used, so that further development—taking into consideration the particular hardware situation—can be done even after the implantation. Experience with a particular pacemaker type in a great number of patients with corresponding clinical pictures thus contributed subsequently to optional further development or improvement of the already implanted system.

The illustration shown on the screen of the communication unit for instance corresponds to a block diagram such as that shown in FIG. 5.

Figure 6A:
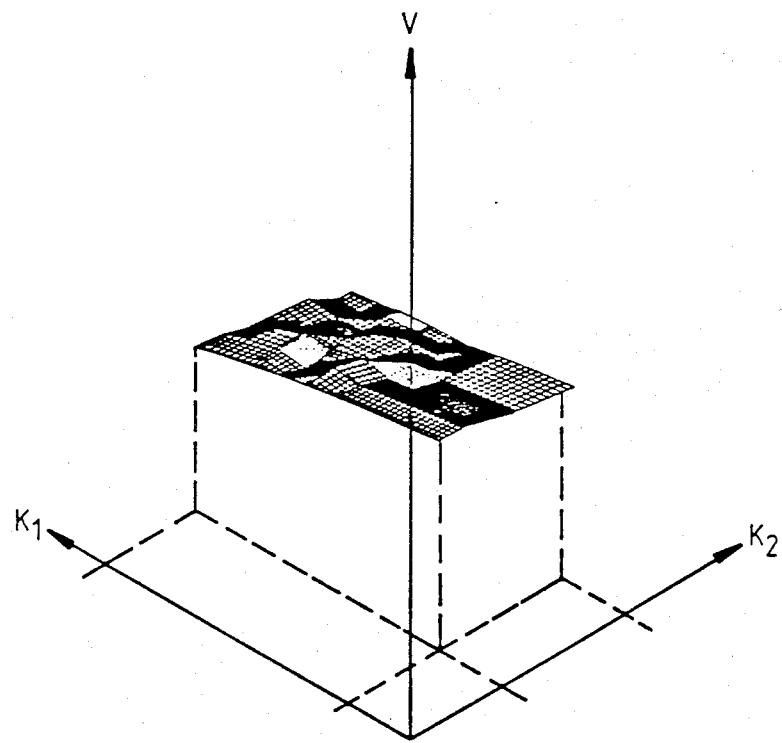
FIGS. 6a6e show various characteristic graphs in three-dimensional views, for explaining different variants of the exemplary embodiment.
Figure 6B:
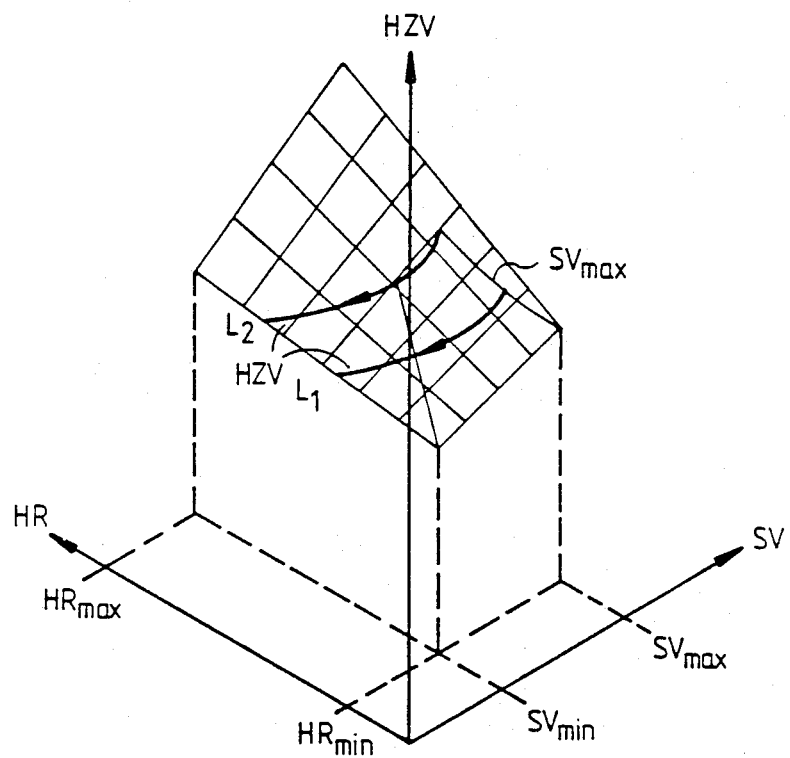
Figure 6C:
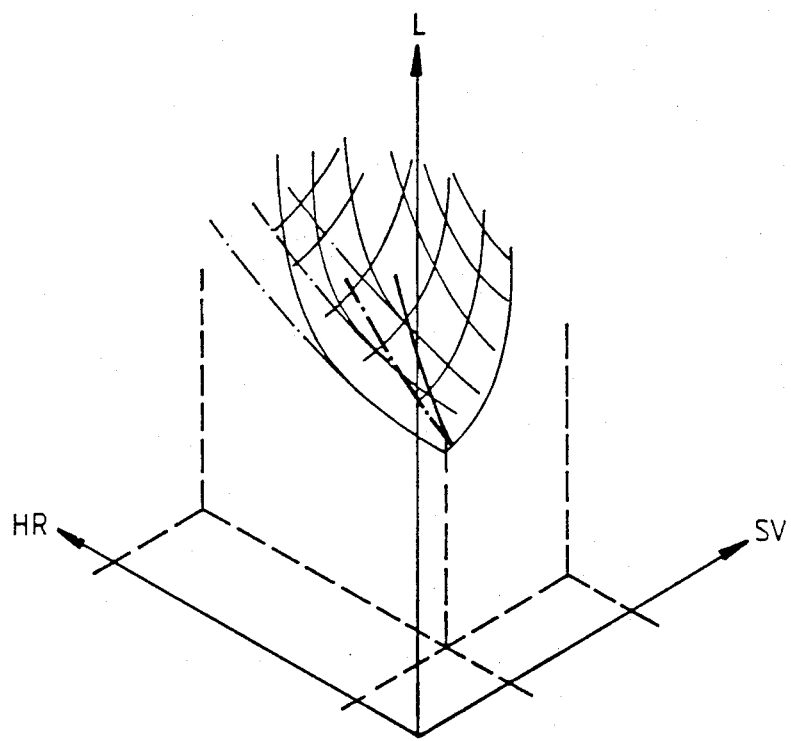
Figure 6D:
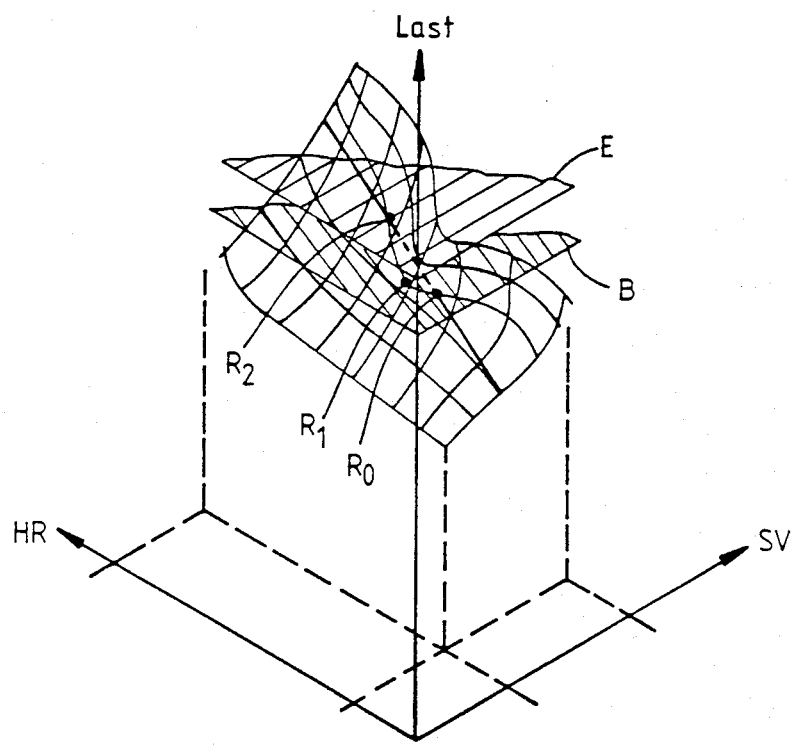

The characteristic fields shown in FIGS. 6a–6c provide examples for relationships, stored in memories having a matrix organization, between variables such as are used in the abovedescribed pacemaker concept. The representation is preferably done in a three-axis coordinate system, so that a perspective graphic illustration in the external control unit can be provided. If only two coordinate axes are used, then the illustration will be in two dimensions. An additional illustration option is provided by superimposing two characteristic fields in one diagram. To standardize the triggering, the characteristic fields selected here are based on three-axis systems, because the associated memory is then designed as a two-dimensional matrix, so that the corresponding numerical values are likewise capable of being illustrated in two dimensions, that is, on the screen, and thus are variable either by means of graphic entries made with a light wand or by numerical input with cursor addressing.

In the characteristic field shown in FIG. 6a, the numerical values K1 and K2 can be two different input variables, which are linked, or they may be one measured variable and one parameter—for example, the current heart rate or the blood temperature. Thus a non-linear characteristic curve of a measured value pickup with temperature correction can be performed.

By superimposing two characteristic fields, a calibration in which the two characteristic fields are matched spatially with one another can be realized, or a regulation of a predetermined strategy, which for instance comprises making the volume between two superimposed characteristic fields, or the dependent variable is sought by means of incremental variation of an independent variable a relative or absolute maximum. In the last-mentioned case, the independent variable represents a measured value, wherein the dependent variables are varied in accordance with the strategy and the variation is monitored in accordance with a differential criterion.

In a further embodiment, one of the axes is the time axis, so that by means of the characteristic fields heart events in the past are stored in memory by means of the characteristic fields and are transferrable out of the heart to the control unit with the same graphic illustration means that also pertain to the rest of the pacemaker system.

Correspondingly, the time-dependent behavior of the pacemaker can be illustrated in the control portion, by graphic means, as a function of heart events, as is known in conventional pacemakers from the representation of the pacing rate as a function of the followup frequency of spontaneous heart actions. While in the control functions the characteristic fields are thus firmly programmed, in the regulation they serve as memories for the variable values, which are used as a basis for the regulating criterion; the regulating operation makes the status of the system graphically clear to the attending physician by means of graphic representation of the current field of the most recently run-through values. By corresponding programming, the system is switchable—as described—at any time between an open-loop control system and a closed-loop control system. This switchover can be done automatically as a function of preceding signals, if a corresponding characteristic field association is provided.

In FIG. 6b, in a further characteristic field, the cardiac output is shown as a function of the heart rate and in [sic] the stroke volume. This characteristic field has particular significance for the controlling of the pacemaker, because the cardiac output is a standard for the performance capacity of the heart, especially since the variation of the heart rate by itself is not a sufficient criterion, if the attainable stroke volume is left out of consideration. The characteristic field shown in FIG. 6b shows the purely mathematical relationship that is attained by calculation, where two different load curves L1 and L2 are plotted on the precondition that a constant physical load must be countered, in the control of the pacemaker, with a likewise corresponding cardiac output. The stroke volume is variably shown between the minimum and maximum physiologically allowable values, and the same is true for the heart rate. For the pacemaker, however, only the heart rate can be influenced, while the stroke volume is established automatically is accordance with the existing adaptability of the heart. That is, it furnishes on the one hand, as a product with the heart rate, a standard for the current performance of the heart, while on the other hand a decrease or increase—with respect to a constant heart rate—is a criterion that the intracorporeal regulating system desires an increase or decrease in the cardiac output, as long as this adaptability is still present in the particular patient.

To enable better evaluation on the part of the physician as to what consequence the individual open- or closed-loop control variables and optionally a correspondingly selected operating characteristic curve have for the control, the illustration of FIG. 6c is provided. Here, in a further characteristic field, the dependency of the stroke volume on the heart rate and on exertion is shown; the axial direction has been selected in accordance with that in the characteristic field of FIG. 6b, to enable simpler comparison. It is demonstrated here that the stroke volume, in the case of restricted adaptability of the heart rate—as shown here—is limited toward higher values, and toward higher frequency values the stroke volume decreases, because the chamber filling decreases, in particular in the ischemic heart. By superimposition of the values of the corresponding diagrams, the operating range of the pacemaker is to be defined, and in the case of automatic adjustment by characteristic field super-imposition, the point of departure is that the external exertion variable must not be allowed to deviate by more than a predetermined amount from the cardiac output, if the performance capacity of the heart is to be adequate to exertion over the long term.

The solid line in the illustration shows that an overly great increase in the heart rate (characteristic curve with slight upward slope with respect to the axis HR) leads to a drop in the cardiac output and is therefore not favorable in the case shown. Contrarily, the plotted course of a characteristic curve is favorable, in the event that the exertion of the particular patient must continue to be limited because of the restricted volumetric adaptation of the heart. If the characteristic field of FIG. 6c extends to higher rates HR, contrarily—as shown in dashed lines—then the operating characteristic curve can be selected flatter toward higher heart rates [and] a region without reduction of the stroke volume is attainable, in which the cardiac output is correspondingly increased. If there are times of spontaneous activity of the heart, then the operating characteristic curve of FIG. 6c is ascertained by ergometric exertion of the patient during spontaneous actions, and in the pacing instance is used accordingly, using the stroke volume as a control variable.

In the case where there is additional knowledge of measurement variables which—as described—enable [sic; word missing] the requirement of the cardiac output on the basis of current physiological exertion data of the heart, a further possibility for control exists, wherein in this case the working points resulting on the basis of the stroke volume that is established as shown in diagram 6c and the working points resulting on the basis of the required cardiac output as shown in FIG. 6b are superimposed, and an average is taken based on the weighted data; however, an allowable rate range can be predetermined, which results from the comparison of the diagrams of FIGS. 6b and 6c, under the aforementioned conditions that the cardiac output and the exertion in the characteristic field should not deviate substantially from one another.

The characteristic field according to FIG. 6c is in particular laid out such that rate ranges in which increasing load [sic; word missing] a reduction of the stroke volume (with respect to the corresponding stroke volume at a higher rate), are to be circumvented, because in such a case a higher rate value leads to a better cardiac performance. These relationships, however, are readily apparent in the characteristic field representation, and the attending physician can make optimal arrangements by using the control unit having the possibility for a graphic display.

An additional favorable application of the characteristic fields shown here is in the graphic monitoring of adaptation of the programmable time constants. Here measured variables that are associated with time constants—for instance thermal regulation of the circulation, taking the blood value into account—are [sic; no remaining verb in sentence]. In this case, with an external abruptly increasing exertion, the rise in the blood temperature is monitored by comparative measurement and chronologically displayed, and the "programmable time constant" contained in the corresponding processing component group is now varied in such a way that the theoretical course resulting therefrom is adapted as much as possible to the actual time behavior, and in the three-axis perspective characteristic field display the variation of one parameter can be taken into account as additional independent variables.

In FIG. 6, with the aid of the diagram known from the foregoing drawing figures, the linkage of the control of the heart rate by means of a plurality of input signals in shown in accordance with an exclusive OR linkage. The illustration is at the same time an example of a system configuration in which the signal processing method is dependent on a signal event itself. The heart rate is influenced first in a manner linked to the stroke volume, as described above. In the case of the arrow 5 shown in the diagram, however, it is presumed that the variation of the stroke volume in the particular patient (or a corresponding variable) is usable only to a limited extent for controlling the heart rate.

In the case of the rate $R_1$, it is assumed that there is an intrusion I, resulting in a rise of the exertion B in the peripheral region of the useful field, without the rate $R_1$ reducing the stroke volume to a value adequate for this exertion. In the case of a heart rate influenced solely by the stroke volume, the rate would attain a maximum value $R_0$, and upon an increase in the exertion would decrease again, because the stroke volume undergoes an intrusion toward the frequency $R_1$, and decreases from $R_0$ on, which in turn leads to another rate reduction. Thus in this case $R_0$ represents the upper rate limitation of the pacemaker.

In order in this case as well to offer the patient a physiologically correct control, a further load-related parameter of the pacemaker (for example, the blood temperature) is additionally utilized for control. The blood temperature picked up is converted in a corresponding characteristic field into the associated exertion level B, which is linked by means of an OR relationship with the output signal of the characteristic field which contains the rate programmed in accordance with a variable correlated with the stroke volume, so that the control of the heart rate is taken over by the blood temperature, if upon attaining a certain temperature level an associated heart rate is not attained. In the graphic display presented to the physician for monitoring, the exertion level as a function of the temperature is represented by a horizontal surface, which shifts by level. If the level exceeds an exertion value that is greater than a corresponding exertion that is adequately covered by the cardiac output resulting at the heart rate stroke volume, then the temperature sensor takes over the task of "guidance", in that the heart rate is now influenced such that the cardiac output is adapted to the direction.

This corresponds to a switchover of the outputs of the characteristic fields in the manner of an OR linkage. The variable linked to the stroke volume now serves with the product of the heart rate for ascertaining the actual cardiac output, and the heart rate is raised enough that the attainable cardiac output is again equivalent to the exertion. This is the case at the rate $R_2$. The control shown by means of superimposition of two physiological parameters results in a relatively rapid runthrough of the rate range from $R_0$ to an $R_2$ in the patient with increasing exertion, so that at all times an adequate cardiac output for the exertion is made available.

Figure 6E:
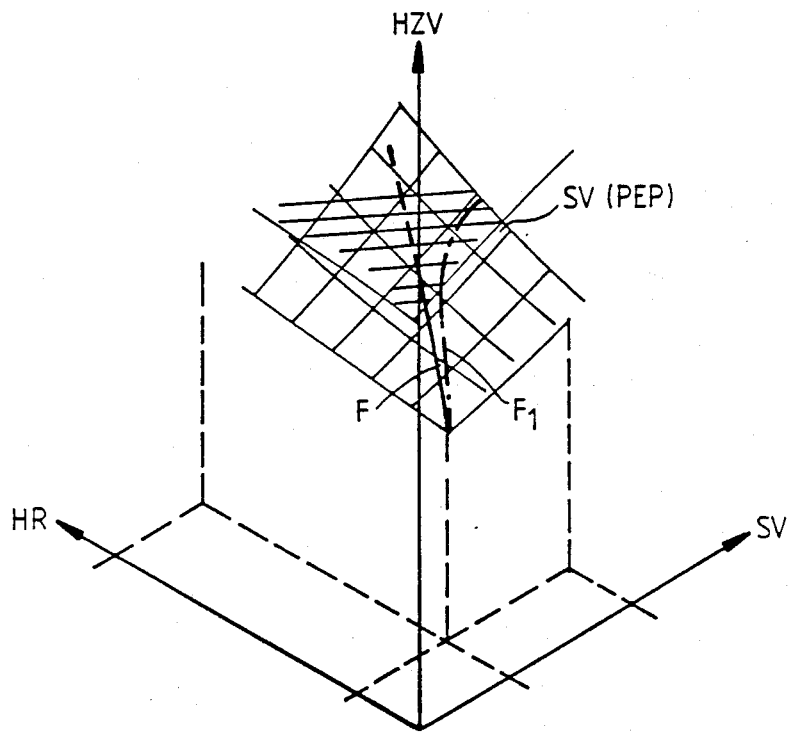

Referring to the diagram shown in FIG. 6e, an exemplary embodiment will be explained, in which the switchover to various physiological parameters for the sake of controlling the heart rate is done not as a function of a picked up parameter, but rather as a function of the heart rate. In the physiological course represented in the diagram shown, a variable characteristic of the stroke volume no longer varies beyond a certain heart rate, even though at higher rates a stroke volume adaptation still takes place. This can for instance happen if the signal PEP (presphygmic period) is also used for the rate control, while LVET (systolic discharge time) is initially not taken into account, but does increase further with increasing exertion. In this case, a control exclusively as a function of PEP would means that the physiological regulation would become effective up to a certain heart rate range. Above this value, an exertion adaptation takes place only by means of a physiological stroke volume adaptation, which in the case of peak exertions can lead to an unsatisfactory adaptation behavior. A changed programming of the characteristic curve (F1) in the operating range that is available does not produce any change here, because with a lower rise in the heart rate as the PEP increases, only the stroke volume adaptation based on LVEP is utilized to a greater extent already at lower rates. In this case (as described for the diagram shown earlier), use is made of the fact that by means of an additional performance-related physiological parameter ascertained in the body of the patient, the heart rate is additionally raised upon exertion whenever the product of the stroke volume and the heart rate is no longer adequate for the physical exertion. To this end, however, a measured variable must then be picked up which is correlated exactly with the current stroke volume, while the characteristic variable PEP picked up here furnishes information for only a portion of the stroke volume adaptation. In that case, a characteristic field is used which as a function of the current heart rate effects a switchover to the control by means of another parameter. The signals PEP and LVEP here form signals picked up by means of acoustic receivers in the heart chamber, these signals being representative for the stroke volume.

Above a predetermined heart rate HR, the heart rate is thus controlled by the blood temperature, so that an additional heart rate increase with increasing exertion is possible, which permits a further heart increase. In this case, by means of a suitable programmed characteristic field which as data contains a linkage instruction for different characteristic fields in programmed form and to this end assures that above a predetermined rate level the blood temperature, at a value that corresponds to a major physical exertion, contributes to the further rate increase, so that the cardiac output is adapted to the actual exertion, and the additional adaptation capability of the stroke volume (which with control by PEP does not need to be ascertained) also forms an additional reserve at higher rates. The blood temperature, for instance as a differential value, will generate an additional programmable relative variation of the heart rate, so that no consideration need be taken of measurement deviations inherent in the absolute values. (An additional measurement of the absolute stroke volume is possible, for example, by electroplethysmographic measurement.)

A control of this kind has the advantage that brief adaptations of the stroke volume do not lead to excessive jumps in the rate, yet nevertheless an additional adaptation of the cardiac performance to exertion is possible in the case of a long-lasting major physical exertion (the blood temperature rises in a delayed manner).

In the case of regulation with the cardiac output as the reference variable, where the current stroke volume is used together with an exertion variable as an address for the rate data in the characteristic field, a corresponding rate increase takes place once again, and LVET or some other stroke-volume-dependent measured variable (preferably impedance cardiography)

should be used, in order to attain the stroke volume adaptation in the range of greater exertion as well. It will be understood that in accordance with signal levels, in the manner described, other signal linkages (open-/closed-loop control) are also variable.

The foregoing description shows that the linkages in terms of measurement technology by means of programming of the system on the one hand exactly determine the technical function of the system and make it into an automatic control or regulation system - but on the other hand, the attending physician can monitor the functioning of the system at any time and intervene as needed by monitoring the memory instructions. The invention is not restricted in its scope to the example described above. Instead, a great many variants are conceivable, which make use of the provisions described even with fundamentally different kinds of embodiments. In particular, the invention is not restricted to realization using discrete logical component groups, but instead can advantageously also be realized with programmed logic—in particular including the use of a microprocessor.

I claim:

1. A cardiac pacemaker, comprising:
   means for applying stimulating pulses to the heart of the patient at a rate determined by a pacing parameter;
   means for detecting a first physiological parameter which is correlated with physical exertion of the patient and producing a first output signal representative of said first physiological parameter;
   a memory having a plurality of memory locations containing data;
   a means for producing a first address signal as a function of said first physiological parameter;
   a means for producing at least one further address signal;
   a means for addressing said plurality of memory locations as a function of said first address signal and said further address signal and for outputting the addressed data as a second output signal;
   circuitry means receiving said first output signal for varying the pacing parameter as a function of said first output signal, said circuitry means being controllable by the addressed data received by said circuitry means.

2. A cardiac pacemaker as defined by claim 1, wherein the data contained in an addressed memory location can be read out and used as said selection control signal.

3. A pacemaker as defined by claim 1, wherein input signals are written in the form of data in addressed ones of said plurality of memory locations.

4. A pacemaker as defined by claim 1, wherein each said second output signal represents polling data which activates auxiliary memories that contain a plurality of data.

5. A pacemaker as defined by claim 4, further comprising an external communication means, and an auxiliary memory which is addressable by said external communication means.

6. A pacemaker as defined by claim 5, wherein said auxiliary memory stores information in the form of data which when accessed become command signals which directly affect at least one operating parameter of said circuitry means.

7. A pacemaker as defined by claim 4, further comprising an external communication means and auxiliary memories which contain data that can be read out by said external communication means.

8. A pacemaker as defined by claim 1, further comprising external control and communication means for individually reading in and out and changing of the data of the individual memory locations of characteristic value memories.

9. A pacemaker as defined by claim 8, wherein said external control and communication means include graphic reproduction means which represent the memory contents as a function of signals forming the addresses.

10. A pacemaker as defined by claim 1, wherein said circuitry means includes a microprocessor means for performing serial processing of information retrieved from said memory.

* * * * *

UNITED STATES PATENT AND TRADEMARK OFFICE
CERTIFICATE OF CORRECTION

PATENT NO. : 4,873,980

DATED : October 17, 1989

INVENTOR(S) : Max Schaldach

It is certified that error appears in the above-identified patent and that said Letters Patent is hereby corrected as shown below:

In the heading of the patent, [73] Assignee, before "Mess-und" insert --BIOTRONIK--.

Signed and Sealed this

Thirtieth Day of October, 1990

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,873,980

DATED : October 17, 1989

INVENTOR(S) : Max Schaldach

It is certified that error appears in the above-identified patent and that said Letters Patent is hereby corrected as shown below:

On the title page, item [73] Assignee: the fullname of the assignee should read as --BIOTRONIK Mess- und Therapiegeräte GmbH & Co. Ingenieurbüro Berlin--.

This Certificate supersedes Certificate of Correction issued October 13, 1990.

Signed and Sealed this

Sixth Day of July, 1993

Attest:

MICHAEL K. KIRK

Attesting Officer

Acting Commissioner of Patents and Trademarks